United States Patent
Goulait

Patent Number: 6,080,347
Date of Patent: *Jun. 27, 2000

[54] METHOD OF MAKING A ELASTICALLY EXTENSIBLE MECHANICAL FASTENING SYSTEM

[75] Inventor: David Joseph Kenneth Goulait, Cincinnati, Ohio

[73] Assignee: The Procter & Gamble Company, Cincinnati, Ohio

[*] Notice: This patent issued on a continued prosecution application filed under 37 CFR 1.53(d), and is subject to the twenty year patent term provisions of 35 U.S.C. 154(a)(2).
Under 35 U.S.C. 154(b), the term of this patent shall be extended for 701 days.

[21] Appl. No.: 08/521,256

[22] Filed: Aug. 30, 1995

Related U.S. Application Data

[63] Continuation of application No. 08/137,566, Oct. 15, 1993, abandoned.

[51] Int. Cl.[7] .............................. B29C 47/00; A41H 37/02
[52] U.S. Cl. ...................... 264/167; 156/66; 156/244.22; 264/251; 264/257; 264/229
[58] Field of Search .............................. 24/442, 446, 447, 24/448, 449, 450, 451, 452; 264/167, 229, 251, 257; 156/66, 244.22

[56] References Cited

U.S. PATENT DOCUMENTS

| | | | |
|---|---|---|---|
| 3,848,594 | 11/1974 | Buell | 128/284 |
| 4,628,709 | 12/1986 | Aeschbach et al. | |
| 4,699,622 | 10/1987 | Toussant et al. | 604/389 |
| 4,846,815 | 7/1989 | Scripps | 604/391 |
| 4,869,724 | 9/1989 | Scripps | 604/389 |
| 4,963,140 | 10/1990 | Robertson et al. | 604/389 |
| 5,032,122 | 7/1991 | Noel et al. | 24/442 X |
| 5,058,247 | 10/1991 | Thomas et al. | 24/448 |
| 5,116,563 | 5/1992 | Thomas et al. | 264/167 |
| 5,133,112 | 7/1992 | Gomez-Acevedo | 24/450 |
| 5,300,058 | 4/1994 | Goulait et al. | |
| 5,361,462 | 11/1994 | Murasaki | 24/452 |

FOREIGN PATENT DOCUMENTS

| | | |
|---|---|---|
| 0233704 | 8/1987 | European Pat. Off. |
| 0532035 A2 | 3/1993 | European Pat. Off. |
| WO 92/04000 | 3/1992 | WIPO |

*Primary Examiner*—Jan H. Silbaugh
*Assistant Examiner*—Mark Eashoo
*Attorney, Agent, or Firm*—Larry L. Huston; E. Kelly Linman; Donald E. Hasse

[57] ABSTRACT

A method of making a mechanical fastening system. The mechanical fastening system is attachable to a complementary receiving surface. The method comprises the steps of providing an elastically extensible substrate and stretching the substrate. Prongs are applied to the substrate while the substrate is stretched. The prongs are joined to the substrate at a base and extend outwardly from the substrate along a shank to an engaging means. The substrate is released, whereby it is allowed to contract.

4 Claims, 1 Drawing Sheet

METHOD OF MAKING A ELASTICALLY EXTENSIBLE MECHANICAL FASTENING SYSTEM

This is a continuation of application Ser. No. 08/137,566, filed on Oct. 15, 1993 now abandoned.

FIELD OF THE INVENTION

The present invention relates to mechanical fastening systems, and more particularly to hook and loop fastening systems.

BACKGROUND OF THE INVENTION

Fastening systems of various types have long been known in the art. One common type of fastening system is the adhesive fastening system. Adhesive fastening systems have long been used on disposable absorbent articles, such as diapers and sanitary napkins.

Adhesive fastening systems, such as tape tabs, are used on diapers to secure such absorbent articles about the waist and torso of the wearer. The diaper may be removed for inspection of the wearer and to be discarded when soiled. Examples of attempts in the art to make adhesive fastening systems for disposable diapers are illustrated by commonly assigned U.S. Pat. No. 3,848,594 issued Nov. 19, 1974 to Buell; U.S. Pat. No. 4,699,622 issued Oct. 13, 1987 to Toussant et al.; and European Patent Application 0,233,704A2 published Aug. 26, 1987 to Buell.

In sanitary napkins, adhesive is used to temporarily and detachably join the garment facing surface of the sanitary napkin to the undergarment of the wearer. Sanitary napkins, like diapers, comprise a liquid pervious topsheet, which faces and contacts the skin of the wearer, a liquid impervious backsheet which is opposed to the topsheet, and an absorbent core intermediate the topsheet and the backsheet. The backsheet has a garment facing surface which is oriented towards and contacts the undergarment of the wearer and a surface opposed thereto which is oriented towards the core. When the sanitary napkin is soiled it is detached from the undergarment of the wearer. A new sanitary napkin is installed and adhesively joined to the undergarment. An example of such adhesive in a sanitary napkin is illustrated by International Patent Publication WO 92/04000 published Mar. 19, 1992 to Papa et al.

One improvement to the fastening systems of such disposable absorbent articles is the use of mechanical fastening systems comprising hook and loop type fastening members. Typically such fastening systems involved two major components, a prong which is joined to and extends outwardly from a substrate. The mechanical fastening system engages a complementary second component, a receiving surface. The receiving surface typically comprises one or more layers of strands or fibers.

A projection of the prong of the fastening system, typically referred to as the "engaging means" penetrates the receiving surface and engages or intercepts strands or fibers of the receiving surface. The resulting mechanical interference and physical obstruction prevent removal of the prong from the receiving surface until separation forces exceed either the peel strength or the shear strength of the fastening system.

Such mechanical fastening systems have been suggested in the art to augment or replace adhesive fastening systems. Mechanical fastening systems used in disposable absorbent articles provide the advantage that the adhesive does not become blocked, and hence inoperable or ineffective, with multiple inspections of the disposable absorbent article or become contaminated by oil from the fingertips of the inspector. Examples of mechanical fastening systems in a disposable diaper are illustrated by commonly assigned U.S. Pat. No. 4,846,815 issued Jul. 11, 1989 to Scripps; U.S. Pat. No. 4,869,724 issued Sep. 26, 1989 to Scripps; and U.S. Pat. No. 4,963,140 issued Oct. 16, 1990 to Robertson et al.

However, to date, the advances and use of such mechanical fastening systems in the art have focused principally upon the prong, such as making it more "skin friendly" (less abrasive) to the wearer, providing a disposal means for the garment when it is soiled, etc. However, little attention has been paid in the art to the substrate to which the prongs of the mechanical fastening system are joined.

The substrates are typically films, such as polyolefins, and are inelastic. However, inelastic substrates provide several disadvantages vis-à-vis elastic substrates when used for the fastening system in a disposable absorbent article. For example, an elastic substrate in a mechanical fastening system used in a disposable absorbent article eliminates, or at least reduces, the size of the elastic waistband. If the substrate of the fastening system can yield, much smaller elastic components can be utilized in the diaper to achieve expansion and fit around the stomach of the wearer. Furthermore, if the fastening system can yield under the stresses of application to the wearer and subsequent wearing, the forces and associated strains can be accommodated by the mechanical fastening system. Accordingly, the remaining materials of the diaper do not have to be as strong, because the stress is not localized at a rigid fastening member. Additionally, a rigid fastening material imparts a dead zone at the point of attachment. This dead zone causes a loss of extension on an elastically extensible waist margin of the diaper and may have a deleterious effect on the fit of the diaper to the wearer. Finally, an extensible substrate for the mechanical fastening system provides more versatility in the design of the diaper. The receiving surface for a fastening system having an extensible substrate can be placed anywhere on the diaper. It is not necessary that the receiving surface be coordinated and juxtaposed with an elastic waistband or other features of the diaper.

Moreover, an extensible substrate provides benefits which extend beyond disposable absorbent articles and which can be more generally applied and appreciated. For example, each prong of a mechanical fastening system having an extensible substrate can operate more independently of the other prongs, due to the inter-prong strain which can be accommodated. Such accommodation prophetically provides greater peel strength and greater shear strength than a fastening system having an inelastic substrate, because more prongs remain engaged on a fastening system having an elastic substrate. Furthermore, the extensible substrate allows for expansion and deformation of the object secured by the mechanical fastening system without exerting undue stresses on the object.

BRIEF SUMMARY OF THE INVENTION

The invention comprises a fastening system for attachment to a complementary receiving surface. The fastening system comprises an array of prongs joined at a base to an elastically extensible substrate and extending outwardly therefrom to an engaging means. The elastically extensible substrate comprises a generally planar sheet of material having an extensibility in any one direction of at least 25 percent, a five second recovery of at least 50 percent, and a spring rate of less than 500 grams per inch of width.

The fastening system may be used in conjunction with a disposable absorbent article such as a diaper, and provide for attachment of the diaper about the waist of the wearer. Alternatively, the fastening system may be used in a sanitary napkin. In a sanitary napkin the elastic substrate of the fastening system may be joined to or integral with the outwardly facing surface of the backsheet. The prongs then provide for attachment of the sanitary napkin to the undergarment of the wearer.

DETAILED DESCRIPTION OF THE INVENTION

Figure 1:
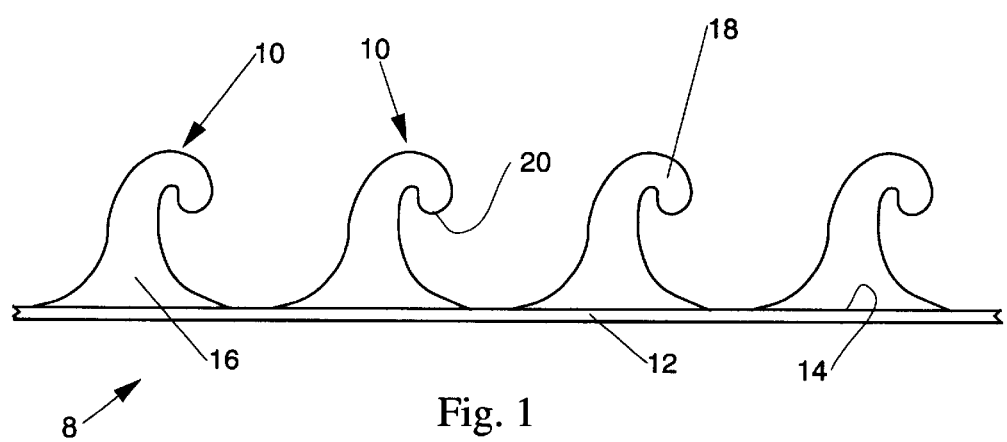
FIG. 1 is a profile view of a fastening system according to the present invention.
Figure 2:
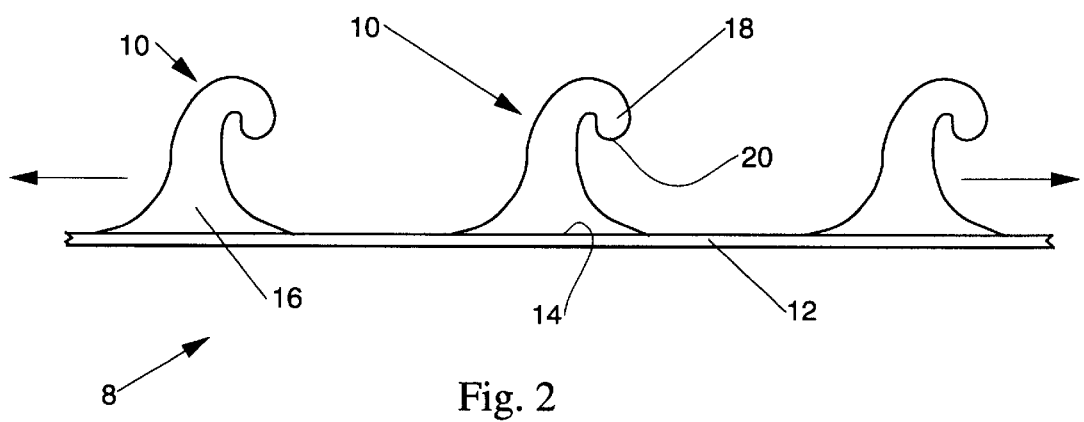
FIG. 2 is a profile view of the fastening system of FIG. 1 showing the substrate in an elastically extended configuration.

The fastening system 8 of the present invention comprises an array of prongs 10. Each prong of the array is joined to the substrate 12, preferably in a predetermined pattern. Each of the prongs 10 has a base 14, a shank 16, and an engaging means 18. The bases 14 of the prongs 10 contact and are joined to the substrate 12, and support the proximal ends of the shanks 16. The shanks 16 project outwardly from the substrate 12 and bases 14. The shanks engaging means 18 terminate at the distal end 20 of the shank 16.

The engaging means 18 projects laterally from the shanks 16 in one or more directions and may resemble a hook-shaped tine. As used herein "lateral" means having a vector component generally parallel to the plane of the substrate 12 at the principal prong under consideration. The projection of an engaging means 18 from a shank 16 in a lateral direction allows the engaging means 18 to be secured to a complementary receiving surface (not shown). The engaging means 18 is joined to, and preferably contiguous with, the distal end 20 of the prong. It will be apparent that the engaging means 18 may be joined to the prong at a position between the base 14 and the distal end 20 of the shank 16. The substrate 12 of the fastening system 8 is elastically extensible.

As used herein, a substrate 12 is considered to be "elastically extensible" if it exhibits a relaxation-extension area ratio greater than or equal to about 0.6, and preferably greater than or equal to about 0.75 when tested as described below. To determine the relaxation-extension area ratio, and, hence whether the substrate 12 is elastically extensible.

The fastening system 8, including both the prongs 10 and substrate 12 is cut to a size of about 6.4 centimeters (gage length) by about 2.54 centimeters (width), if the prongs 10 are left attached to the substrate 12. If the fastening system 8 to be tested is too small to yield the preferred test specimen size, a smaller test specimen sample may be tested, providing the aforementioned aspect ratio is maintained.

The elastic extensibility may be measured with a Model 1122 tensile machine made by the Ingstron Engineering Corporation of Canton, Mass. Preferred jaws for this tensile machine are pneumatic action, coated, light duty flat faced jaws, Ingstron Model No. 3B. The sample to be tested is mounted in the tensile machine with the principal axis of elongation oriented in the tensile machine extension direction. The sample is inserted into each jaw only a distance sufficient to prevent tearing out of the jaws upon the application of the tensile force.

The jaws are separated, without tensile loading the sample, until it is taut. All wrinkles, folds, and the like should be removed. This defines the original jaw position of the sample.

The jaws are separated at a constant rate of about 100 centimeters per minute until an elongation of about 25 percent (1.25 times the original gage length) is reached. This procedure produces an extension stress—strain curve from the original gage length and jaw position to the extended position, and having the stress vector along the vertical axis and the strain vector along the horizontal axis. The area under this curve is calculated and hereinafter referred to as $A_1$. A suitable means for calculating the area under this curve is with a computer program such as is available by Laboratory MicroSystems, Inc. of Troy, N.Y., under the name Mechanical Test Package.

The jaws are then returned to the original jaw position at a constant rate of about 100 centimeters per minute. This defines a relaxation stress—strain curve from the extended position to the original gage length. The area under this stress—strain curve is also calculated and hereinafter referred to as $A_2$. The ratio of the area of the relaxation stress—strain curve to the area of the extension stress—strain curve, $A_2$ divided by $A_1$, is then found and is hereinafter referred to as the relaxation-extension area ratio. The mechanical fastening system 8 is considered elastically extensible if the relaxation-extension area ratio is greater than or equal to about 0.6. However, as noted above, the relaxation-extension area ratio is preferably greater than or equal to about 0.75.

The sample may be tested in any direction. However, it is understood that the direction of extensibility is preferably aligned with the azimuthal orientation of the engaging means 18 of the prongs 10.

Preferably the substrate 12, with the array of prongs 10 joined thereto, exhibits a spring rate of less than 500 grams per inch of width of substrate 12, and more preferably a spring rate less than 1,000 grams per inch of width of substrate 12. If all of the engaging means 18, or at least a majority thereof, of the prongs 10 are oriented in the same azimuthal direction, preferably the spring rate and relaxation-extension area ratio are measured in that direction. However, a substrate 12 according to the present invention is considered to meet the elastic extensibility and spring rate criteria set forth above if such measurements occur in any direction lying within the plane of the substrate 12.

The spring rate may be measured using the same tensile machine described above. Of course, it will be understood by one skilled in the art that if a sample having one inch of width is not available, a sample of lesser width may be tested and the results normalized to a one inch width.

If the spring rate of the substrate 12 is too low, and hence the material has excessive strain at a given force application, an insufficient number of prongs 10 may engage the receiving surface. The elastic extensibility, particularly the strain, of the fastening system 8 will be limited by the size and density of the prongs 10. The bases 14 of the prongs 10 make a footprint on the substrate 12. The portion of the substrate 12 at the footprint of the bases 14 of the prongs 10 is not elastically extensible, due to the prong 10 material being generally inextensible within the plane of the substrate 12.

Accordingly, it is desired, but not necessary, that the prongs 10 comprising the array be bilaterally staggered. A bilaterally staggered array of prongs 10 provides for a generally biaxial distribution of the applied loads when the fastening system 8 is in use. Additionally, a bilaterally staggered array of prongs 10 may have a greater density than if the prongs 10 are arranged in rows.

Alternatively, if the prongs 10 are arranged in rows, and substantially conform to a grid, the spaces in the substrate 12 intermediate the prongs 10 can elastically expand in rows generally perpendicular to the applied forces. Such rows will be generally straight if the prongs 10 are arranged on a grid, but will be sinuous if the prongs 10 are bilaterally staggered.

The substrate 12 can comprise any suitable material and either be pre-stretched as is well known in the art, or may be a zero-strain material as is well known in the art. Suitable materials for the substrate 12 include polyolefins, natural rubbers, and preferably foams, such as polyolefins, natural rubbers, and preferably foam, such as polyurethane foam available from General Foam of Paramus, N.J. The substrate 12 may have a thickness of about 1.5 millimeters to 3.0 millimeters, and a basis weight of about 0.02 to 0.05 grams per square centimeter. A particularly suitable substrate 12 is a laminate comprising a Kraton-based elastomer, such as Exxon 500 made by the Exxon Chemical Company of Houston, Tex. and P-8 nonwoven material made by Veratec of Walpole, Mass. The preferred laminate has a central elastomer lamina between two outboard nonwoven laminae. Alternatively, a dual ply laminate having a nonwoven lamina and an elastomer lamina may be utilized.

If desired, the substrate 12 may be prestrained. For example, the substrate 12 may have a density of 80 prongs 10 per square inch. The substrate 12 may be later activated (such as by heat shrinking) to contract to a density of 320 prongs 10 per square inch. A prestrained substrate 12 has the advantage of providing a preload in the product. The substrate 12 may be bilaterally contracted, or contracted in a single direction. Bilateral contraction has the advantage that the prongs 10 may be freeformed or printed, as described below, at a particular density then the substrate 12 contracted to a higher density. Alternatively, unilateral contraction has the advantage that the pitch of the prongs 10 may vary in two orthogonal directions. If it is desired to use a prestrained substrate 12, a suitable material is a heat shrink elastomeric film, made by the Exxon Chemical Company of Houston, Tex. Alternatively, a substrate 12 which is not thermally activated may be pre-stretched, the prongs 10 applied thereto, then released and allowed to contract.

The prongs 10 may be manufactured by any of several methods well known in the art. Suitable methods include extrusion, cutting of individual loops and preferably being free formed. As used herein, the term "free formed" refers to a structure which is not removed from a mold, cavity, or extrusion die in solid form or with a defined shape. The free formed prongs 10 are deposited onto the extensible substrate 12 in a molten, preferably liquid state, and solidified by cooling until rigid and preferably freezing into the desired structure and shape. A free formed mechanical fastening system 8 may be produced in accordance with the teachings of commonly assigned U.S. Pat. No. 5,085,247 issued Oct. 22, 1991 to Thomas et al.; U.S. Pat. No. 5,116,563 issued May 26, 1992 to Thomas et al.; or U.S. Pat. No. 5,230,851 issued Jul. 27, 1993 to Thomas, the disclosures of which three patents are incorporated herein by reference for the purpose of showing particularly preferred methods of manufacturing a fastening system 8 suitable for use according to the present invention and having free formed prongs 10.

If desired, the prongs 10 may be incorporated into a disposable absorbent article such as a diaper. The diaper may be made according to the teachings of U.S. Pat. No. 3,860,003 issued Jan. 14, 1975 to Buell, or according to the teachings of the aforementioned U.S. Pat. Nos. 4,869,724; 4,846,815; or 4,963,140, all of which patents are incorporated herein by reference for the purpose of showing how a fastening system 8 according to the present invention may be advantageously incorporated into a disposable absorbent article such as a diaper.

Such a diaper has a liquid pervious topsheet, a liquid impervious backsheet joined to the topsheet, and an absorbent core intermediate the topsheet and the backsheet. The backsheet has one outwardly oriented face, typically referred to as the garment facing surface due to its orientation towards the wearer's outer garments, and a core facing surface opposed thereto.

The mechanical fastening system 8 is juxtaposed with one waist margin of the diaper, preferably so that the prongs 10 and engaging means 18 are near the rear waist margin. The complementary receiving surface may be joined to the outwardly facing surface of the backsheet juxtaposed with the other waist margin, preferably the front waist margin. The diaper is drawn between the legs of the wearer and the prongs 10 of the mechanical fastening system 8 brought around the waist of the wearer and engaged with the receiving surface.

The diaper may have a detachable belt, as illustrated by commonly assigned U.S. Pat. No. 4,964,860 issued Oct. 23, 1990 to Gipson et al. The detachable belt may be made of extensible material comprising the substrate 12 according to the present invention and have the prongs 10 attached thereto for securing the belt and diaper about the waist of the wearer. Either this type of fastening system 8 or the type of fastening system 8 having tape tabs juxtaposed with the waist margin of the diaper is suitable for use within the scope of the present invention.

Alternatively, the mechanical fastening system 8 according to the present invention may be utilized with a sanitary napkin to either replace or augment the fastening adhesive, commonly used in the art and described above. A suitable sanitary napkin is preferentially made in accordance with commonly assigned U.S. Pat. No. 5,009,653 issued Apr. 23, 1991 to Osborn, III, which patent is incorporated herein by reference for the purpose of showing a particularly suitable sanitary napkin for use with the present invention.

A suitable sanitary napkin has a liquid pervious topsheet, a liquid impervious backsheet joined to the topsheet and an absorbent core intermediate the topsheet and the backsheet. The backsheet may be elastically extensible as described above and the bases 14 of the prongs 10 of the mechanical fastening system 8 joined to the backsheet. In such an embodiment the substrate 12 of the mechanical fastening system 8 is integral with the backsheet of the sanitary napkin. Alternatively, the elastically extensible substrate 12 of the mechanical fastening system 8 may be joined to a backsheet according to the prior art. It will be apparent to one skilled in the art, it is preferred the prongs 10 be printed directly onto an elastically extensible backsheet so that the substrate 12 and elastically extensible backsheet are integral. The sanitary napkin has a longitudinal centerline. In such an execution, the substrate 12 of the mechanical fastening system 8 can double as the liquid impervious backsheet of the sanitary napkin. The prongs 10 are joined to the garment facing surface of the backsheet and extend outwardly therefrom to engage the undergarment of the wearer.

The disposable absorbent articles such as diapers and sanitary napkins may comprise a longitudinal centerline which generally bisects the standing wearer into left and right body halves and is generally parallel the longitudinal side margins of the absorbent article. The disposable absorbent articles further comprise a lateral centerline which lies within the plane of the disposable absorbent articles and is orthogonal to the longitudinal centerline and is generally aligned with the wearer's left to right directions as the disposable absorbent article is worn.

The prongs 10 may be generally parallel the longitudinal centerline of the sanitary napkin, and oriented towards the lateral centerline. Alternatively, if the engaging means 18 of the prongs 10 are oriented in a nonlongitudinal direction, the backsheet may be generally elastically extensible in a direction parallel the orientation of the engaging means 18 of the prongs 10 on the garment facing surface of the backsheet. Alternatively, the prongs 10 of the fastening system 8 may be arranged in quadrants as disclosed in commonly assigned U.S. patent application Ser. No. 07/988,541 filed Dec. 10, 1992 in the names of Goulait et al., which patent application is incorporated herein by reference.

If desired, the sanitary napkin may be provided with laterally oriented flaps as disclosed in commonly assigned U.S. Pat. No. 4,589,876 issued May 20, 1986 to Van Tilburg and U.S. Pat. No. 4,687,478 issued Aug. 18, 1987 to Van Tilburg, which patents are incorporated herein by reference for the purpose of showing flaps. The flaps may be made laterally extensible and comprise the substrate 12 of the fastening system 8 according to the present invention. The prongs 10 of the fastening system 8 may be applied to the backsheet coextensive side of the flaps. Preferably the prongs 10 are generally parallel the lateral centerline of the sanitary napkin and oriented inwardly toward the longitudinal centerline of the sanitary napkin.

In another execution, the fastening system 8 according to the present invention may be used as an extensible wrap. Extensible wraps are commonly used for athletic purposes i.e., to support joints, such as knees, or muscles, such as hamstrings, during athletic events. Extensible wraps, commonly known as Ace brand bandages, are usually elongate, i.e., relatively long and narrow. If desired, an extensible wrap may be made according to the present invention by supplying the substrate 12 with prongs 10 juxtaposed with one end for attachment to the wrap or, alternatively, may have prongs 10 throughout its entire length. If the prongs 10 are supplied throughout the entire length of the extensible substrate used for the wrap, the user may select only as much wrap is necessary for his or her particular injury and body size. The user may wind a sufficient quantity of the wrap about the body part, and then cut off the excess, so that the athletic wrap is custom fit to the size of the user and has the prongs 10 distributed throughout or substantially throughout for more uniform engagement.

It will be apparent other executions and embodiments are possible, all of which are within the scope of the appended claims.

What is claimed is:

1. A method of making a fastening system attachable to a complementary receiving surface, said method comprising the steps of:

providing a substrate, said substrate being elastically extensible;

stretching said substrate to impart a strain thereto;

applying prongs to said substrate while said substrate is stretched, said prongs being joined to said substrate at a base and extending outwardly from said substrate along a shank to an engaging means; and releasing the strain imparted to said substrate due to said stretching said substrate, whereby it is allowed to contract.

2. The process according to claim 1 wherein said step of stretching said substrate comprises bilaterally stretching said substrate.

3. The process according to claim 1 whereby said prongs have a pitch in each of two orthogonal directions and said step of stretching said substrate comprises unilaterally stretching said substrate so that said pitches vary in each of said two orthogonal directions.

4. The process according to claim 1 wherein said step of applying said prongs to said substrate comprises depositing free-formed prongs onto said substrate.

* * * * *